United States Patent [19]
Shephard

[11] 4,102,907
[45] Jul. 25, 1978

[54] DESULFINYLATION PROCESS FOR PREPARING ANDROSTA-4,9(11)-DIENE-3,17-DIONE

[75] Inventor: Kenneth P. Shephard, Portage, Mich.

[73] Assignee: The Upjohn Company, Kalamazoo, Mich.

[21] Appl. No.: 775,128

[22] Filed: Mar. 7, 1977

[51] Int. Cl.$^2$ .............................................. C07J 5/00
[52] U.S. Cl. ............................ 260/397.3; 260/397.45; 260/239.5
[58] Field of Search ......................... 260/397.3, 397.4

[56] References Cited

U.S. PATENT DOCUMENTS 3,065,146  11/1962  Sih et al. ................................ 195/51

Primary Examiner—Elbert L. Roberts
Attorney, Agent, or Firm—Bruce Stein

[57] ABSTRACT

The present invention discloses a process for the production of -androsta-4,9(11)-diene-3,17-dione-type compounds from 9α-hydroxyandrostenedione-type compounds by forming a sulfinate ester at $C_9$ followed by desulfination.

25 Claims, No Drawings

DESULFINYLATION PROCESS FOR PREPARING ANDROSTA-4,9(11)-DIENE-3,17-DIONE

BACKGROUND OF THE INVENTION

Androstenedione is a $C_{19}$ steroid of the formula:

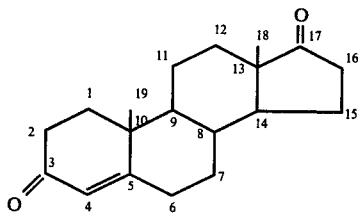

Androsta-4,9(11)-diene-3,17-dione refers to androstenedione with a double bond between carbon atoms 9 and 11. Androsta-4,9(11)-dienes 3,17-dione type compounds refer to steroids within the scope of formula III:

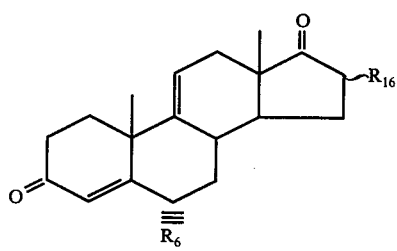

$R_6$, $R_{16}$ and ~ are defined infra.

The -androsta-4,9(11)-diene-3,17-dione-type compounds (III) are useful for producing pharmaceuticals, in particular testosterone derivatives. For example, androsta-4,9(11)-diene-3,17-dione (III) is converted to 3-(N-pyrrolidinyl)androsta-3,5,9(11)-trien-17-one to protect the $C_3$ ketone by the process disclosed by F. W. Heyl and M. E. Herr in J. Am. Chem. Soc. 77, 488 (1955). This protected steroid is converted to 17β-hydroxy-17-methyl androsta-4,9(11)-diene-3-one by a Grignard reaction with methylmagnesium bromide and subsequent alkaline hydrolysis. See M. E. Herr et al., J. Am. Chem. Soc. 78, 500 (1956). This methyltestosterone derivative is then converted to 9α-fluoro-11β,17β-dihydroxy-17-methyl androsta-4-ene-3-one (fluoxymesterone, Halotestin ®) which is a commercially marketed steroid, by the process of U.S. Pat. No. 3,118,880, Example 2.

The $\Delta^{9(11)}$-steroids have been prepared from both 11β-hydroxy steroids and 9α-hydroxy steroids. George G. Hazen and D. W. Rosenburg, J. Org. Chem. 29, 1930 (1964); D. Taub et al., J. Am. Chem. Soc. 82, 4102 (1960); E. M. Chamberlin, J. Org. Chem. 25, 295 (1960); T. Reichstein, U.S. Pat. No. 2,409,798, Drake, U.S. Pat. No. 3,005,834, and Great Britain Pat. No. 1,198,749 all disclose synthesis of $\Delta^{9(11)}$-steroids from 11β-hydroxy steroids. The papers by Hazen, Taub, and Chamberlin all disclose using 11β-hydroxy corticoids to form the corresponding $\Delta^{9(11)}$-corticoids. U.S. Pat. Nos. 2,409,798 (Example 3),3,005,834 (Example 35) and Great Britain Pat. No. 1,198,749 (Example 1) disclose the use of 11β-hydroxy androstenes to produce $\Delta^{9(11)}$-androstenes.

While 11β-hydroxy steroids have been used to synthesize the corresponding $\Delta^9(11)$-steroids, the process of the present invention involves sulfinylation then desulfinylation of 9α-hydroxyandrostenedione-type steroids (I) to form the corresponding androsta4,9(11)-diene-3,17-dione-type steroids (III).

$\Delta^{9(11)}$-Steroids have previously been prepared from the corresponding 9α-hydroxy steroids.

J. Fried et al., Tetrahedron Letters, 13, 849 (1965) disclosed the use of thionyl chloride in pyridine for forming $\Delta^{9(11)}$-steroids from the corresponding 9α-hydroxy tetracyclic triterpene in approximately an 80% yield. C. J. Sih, U.S. Pat. No. 3,065,146 also disclosed using thionyl chloride in pyridine. U.S. Pat. No. 3,065,146 (Example 7, paragraph 1) discloses the preparation of $\Delta^{9(11)}$-dehydroprogesterone. Paragraph 2 states: "In the same manner, following the procedure of example 7...9α-hydroxy-$\Delta^4$-androstene-3,17-dione . . . (is) converted to . . . $\Delta^{4,9(11)}$-androstene-3,17-dione . . ."

No physical data is given for the product, $\Delta^{4,9(11)}$-androstene-3,17-dione. The applicant has performed this reaction obtaining the product in approximately 50% yield. See Preparations 1 thru 3. The reaction produces a 50—50 mixture of the isomeric $\Delta^{9(11)}$- and the $\Delta^8$-olefins. The highest yield obtained of the $\Delta^{9(11)}$-isomer was 55.5% (Example 3). These isomeric olefins had the same $R_f$'s on TLC and could not be separated by crystallization. In addition to the very difficult if not impossible separation problem there is the obvious problem that one obtains only approximately 50% of the desired product.

U.S. Pat. No. 3,005,834 discloses transformation of 9α-hydroxy steroids to $\Delta^{9(11)}$steroids by reaction with an N-haloamide or N-haloimide under anhydrous conditions, in a base, with anhydrous sulfur dioxide. Examples 27 and 28 disclose transformation of 9α-hydroxyprogesterone with yields of 30.3% and 72.2%, respectively. Bromine, sulfur dioxide and an organic base produce the same result, as does an N-haloamide, sulfur dioxide and an organic base, see Great Britain Pat. No. 1,198,749. This process was tested on 9α-hydroxyandrostenedione (I), see Preparations 4 through 6. GC analysis indicates that the product is a mixture of androsta-4,9(11)-diene-3,17-dione (III) and androsta-4,8-diene-3,17-dione. The problem with this process is that the androsta-4,9(11)-diene-3,17-dione (III) isomer makes up at best approximately 65% of the reaction product.

Therefore, the prior art discloses various methods to produce $\Delta^{9(11)}$-steroids from 9α-hydroxy steroids. Preparations 1 through 6 show that when these processes were applied to 9α-hydroxyandrostenedione (I) they produced at best a 65-35 mixture and usually a 50—50 mixture of androsta-4,9(11)-diene-3,17-dione (III) and androsta-4,8-diene-3,17-dione. These isomeric olefinic steroids are very difficult, expensive, and impractical to separate at best. The process of the present invention transforms 9α-hydroxyandrostenedione-type compounds (I) to the corresponding androsta-4,9(11)-diene-3,17-dione-type compounds (III) in virtually quantitative yields (greater than 85%) with a ratio for androsta-4,9(11)-diene-3,17-dione (II) to androsta-4,8-diene-3,17-dione of approximately 98 to 2. This very high yield and high ratio is most surprising and unexpected in view of the prior art methods and is highly advantageous from a commercial point of view.

BRIEF DESCRIPTION OF THE INVENTION

The definitions and explanations below are for the terms as used throughout the entire patent application including both the specification and the claims.

$R_6$ is a hydrogen or fluorine atom or methyl group.

$R_{16}$ is a hydrogen atom or methyl group.

$\sim$ indicates the attachment of the $R_{16}$ group is in the $\alpha$ or $\beta$ configuration.

$\Delta^{9(11)}$ refers to the double bond between carbon atoms 9 and 11 in the steroid.

R is alkyl of 1 thru 4 carbon atoms; or phenyl substituted with 0-3 substituents which may be the same or different and are selected from the group consisting of halogen atoms, or methyl, ethyl, or nitro groups.

X is a chlorine or bromine atom.

Support catalyst is silica gel or alumina.

All temperatures are in degrees centigrade.

TLC refers to thin layer chromatography.

GC refers to gas chromatography.

SSB refers to a mixture of isomeric hexanes.

p-TSA refers to p-toluenesulfonic acid (p-methylphenylsulfonic acid).

DMF refers to dimethylformamide.

THF refers to tetrahydrofuran

Disclosed is a chemical process for the preparation of a steroid of the formula:

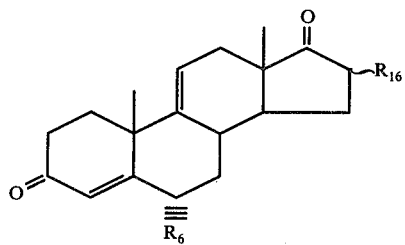

III which comprises
(1) sulfinylating a 9α-hydroxy steroid of the formula:

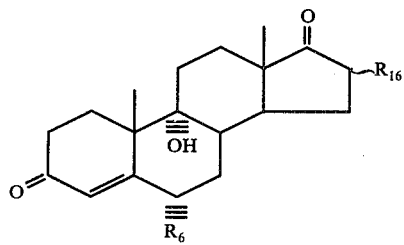

I with a sulfinylating agent of the formula R—SO—X to form a sulfinate ester of the formula:

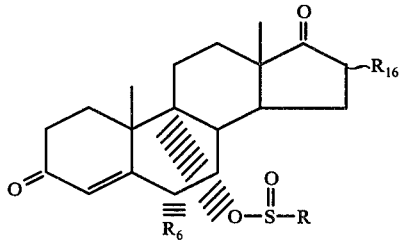

II and (2) desulfinylating the sulfinate ester (II) by heating to at least 40° in the presence of a support catalyst and an acid whose pKa is less than or equal to 5.0. $R_6$, $R_{16}$, $\sim$, R, X, and support catalyst are defined above.

Also disclosed is a chemical process for the preparation of a sulfinate ester of the formula:

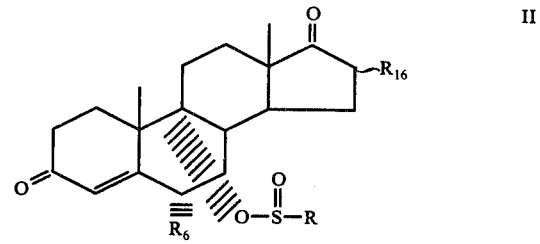

II which comprises sulfinylating a 9α-hydroxy steroid of the formula:

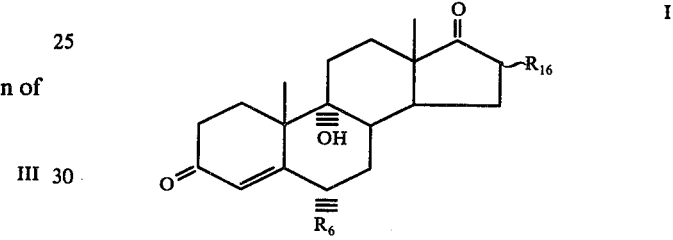

I with a sulfinylating agent of the formula R—SO—X. $R_6$, $R_{16}$, $\sim$, R, and X are defined above.

Further disclosed is a chemical process for the preparation of a steroid of the formula:

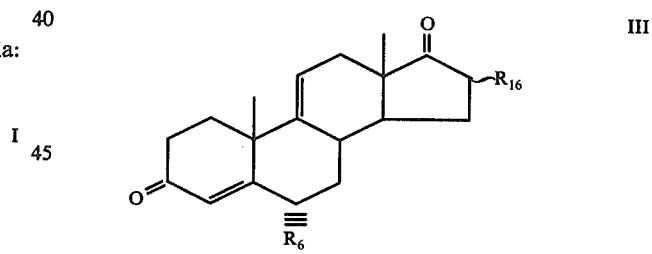

III which comprises desulfinylating a sulfinate ester of the formula:

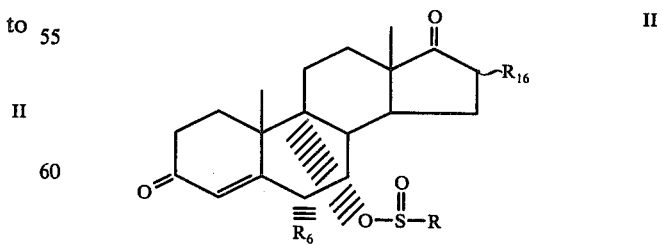

II by heating to at least 40° in the presence of a support catalyst and an acid whose pKa is less than or equal to 5.0 $R_6$, $R_{16}$, $\sim$, and support catalyst are defined above.

Disclosed is a sulfinate ester of the formula:

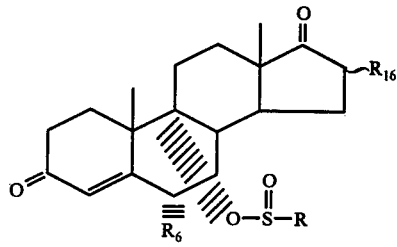

$R_6$, $R_{16}$, ~, and R are defined above.

DETAILED DESCRIPTION OF THE INVENTION

The process of the present invention for preparation of a steroid of the formula:

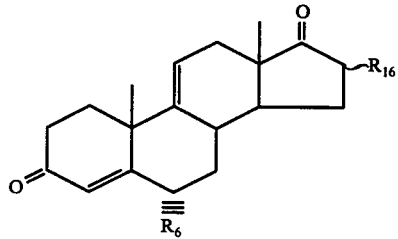

comprises sulfinylating a 9α-hydroxy steroid of the formula:

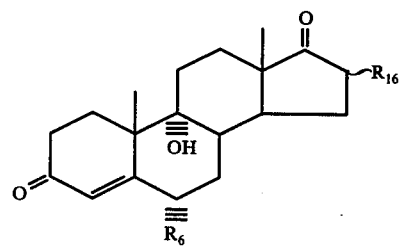

with a sulfinylating agent of the formula R—SO—X to form a sulfinate ester of the formula:

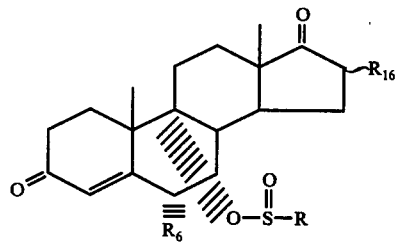

and desulfinylating the sulfinate ester (II) by heating to at least 40° in the presence of a support catalyst and an acid whose pKa is less than or equal to 5.

The process of the present invention may be more fully understood by examining the process as set forth in Chart A.

CHART A

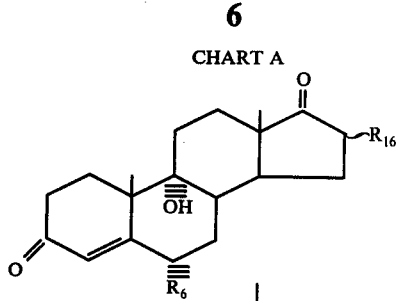

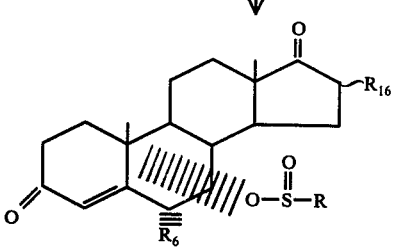

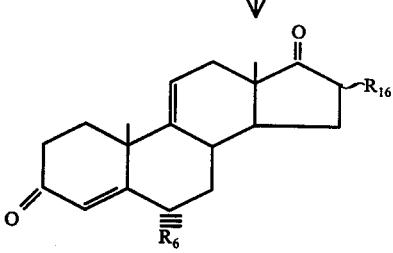

The reactant for the process of the present invention is the 9α-hydroxy steroid of formula I:

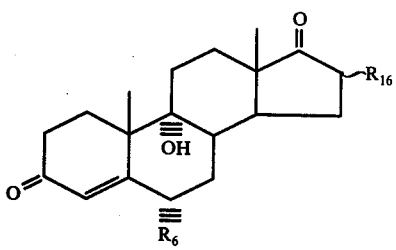

$R_6$ is a hydrogen or fluorine atom or methyl group. $R_{16}$ is a hydrogen atom or methyl group. ~ indicates the attachment of the $R_{16}$ group is in the α or β configuration.

The 9α-hydroxy steroid (I) is sulfinylated with a sulfinylating agent of the formula R—SO—X. R is alkyl of 1 through 4 carbon atoms; or phenyl substituted with 0–3 substituents which may be the same or different and are selected from the group consisting of halogen atoms, or methyl, ethyl, or nitro groups. Examples of alkyl of 1 thru 4 carbon atoms are methyl, ethyl, propyl, butyl, and isomers thereof. Examples of phenyl substituted with 0–3 substituents which may be the same or different and are selected from the group consisting of halogen atoms or methyl, ethyl, or nitro groups are phenyl, p-methylphenyl, p-chlorophenyl, 2,4-dinitrophenyl, 2,4-dimethylphenyl, and 2-methyl-4-chlorophenyl. X is a chlorine or bromine atom. It is preferred that the sulfinylating agent be selected from the group consisting of phenylsulfinyl chloride, p-methylphenylsulfinyl chloride, or p-chlorophenylsulfinyl chloride. It is most preferred that the sulfinylating agent be phenylsulfinyl chloride.

The 9α-hydroxy steroid (I) is dissolved in an organic base such as pyridine, collidine or lutidine. The sulfinylating agent (R—SO—X) is added to the steroid with cooling. Solvents suitable for the sulfinylating reaction include benzene, methylene chloride, chloroform, SSB, THF, and xylene. The reaction mixture is stirred and the reaction is followed by TLC until completion, usually less than 1 hour. The reaction is usually and most simply performed at room temperature, however, temperatures from 0° to 100° are acceptable.

Upon completion of the sulfinylation reaction as measured by TLC, the reaction mixture is worked up by adding water and neutralizing the organic base present with and acid such as hydrochloric or sulfuric acid. At this point the sulfinate ester (II) can be isolated and purified or it can be desulfinylated without isolation. It is preferable to carry on the reaction without isolation and purification of the intermediate sulfinate ester (II).

The water added hydrolyzes any excess sulfinylating agent to the corresponding sulfinic acid. If this acid is not thoroughly washed out at this time it will cause desulfinylation in the subsequent step without further addition of an acid whose pKa is less than or equal to 5.0. See Example 4 where no p-TSA was added.

The desulfination of the sulfinate ester (III) occurs by heating the sulfinate ester (II) to at least 40° in the presence of a support catalyst and an acid whose pKa is less than or equal to 5.0 while stirring.

Suitable solvents for the desulfination reaction include non-basic organic compounds such as chloroform, benzene, toluene, xylene, methylene dichloride, carbon tetrachloride, chlorobenzene, tetrachloroethylene, trichloroethylene, 1,1,1-trichloroethane, and 1,1,2-trichloroethane.

The desulfination reaction does occur at room temperature (about 25°) but the rate of reaction is so slow as not to be practical. Therefore, the reaction mixture is heated to at least 40° and in the temperature range of 40° to 130°.

The support catalyst is either silica gel or alumina. If the support catalyst contains acid impurities, these may be sufficient for the desulfination reaction and additional acid may not have to be added. See Example 4 where no p-TSA was added.

The acid necessary for the desulfination reaction has a pKa less than or equal to 5.0. The pKa of an acid is defined as the negative logarithm (to the base 10) of the dissociation constant, Ka, for the dissociation of the acid, HA.

$$HA = H^+ + A^-$$

$$Ka = \frac{[H^+][A^-]}{[HA]}$$

$$pKa = -\log Ka$$

See the Condensed Chemical Dictionary, Eighth Edition, G. G. Hawley, Van Nostrand Reinhold Co., 1972, p. 698 and Physical Chemistry, Second Edition, F. Daniels and R. A. Alberty, John Wiley & Sons, Inc., 1961, pp. 428-9.

The thermodynamic dissociation constant, Ka, is dependent on temperature and the solvent. See Daniels and Alberty, supra, p. 429. Therefore, in the present invention a pKa less than or equal to 5.0 refers to the pKa at 25° in distilled water.

Various acid catalysts are suitable to increase the rate of the reaction. As stated above even minor acid impurities in the silica gel are sufficient to increase the rate of the reaction sufficiently to be of commercial significance. Mineral acids such as hydrochloric and hydrobromic may be used, preferably phenylsulfonic acid, p-TSA and p-chlorophenylsulfonic acid. It is preferred that the acid be p-TSA. In the situation where an acid (mineral or organic) is added, the addition takes place when the support catalyst is added.

Alternatively, the acid source for the desulfination may be supplied by the hydrolysis of the excess sulfinylating agent. The sulfinylating agents of the formula R—SO—X in the presence of water hydrolyze to form sulfinic acids (R—SO—H). These sulfinic acids can effectuate the desulfination reaction when present. If an excess of the sulfinylating agent is present and water is added during the reaction or work up, sulfinic acids are produced. These sulfinic acids then participate in the desulfinylation reaction and other acids do not have to be added. See Example 4 where silica gel was added to the sulfinate ester (II) but no acid was added.

The reaction mixture, sulfinate ester (II), support catalyst and acid are refluxed until the reaction is complete as measured by TLC, approximately 2 to 3 hours. Upon completion of the desulfinylation reaction, the mixture is filtered to remove the support catalyst (silica gel or alumina). The filtrate is washed successively with distilled water, sodium bicarbonate solution and distilled water. After drying the filtrate is concentrated to dryness under reduced pressure and the resulting solids crystallized to obtain the androsta-4,9(11)-diene-3,17-dione-type compound (III).

The 9α-hydroxyandrostenediones within the scope of formula I are either known to those skilled in the art or can readily be prepared by methods well known to those skilled in the art from readily available known compounds.

The sulfinylating agents within the scope of formula R—SO—X are either known to those skilled in the art or can readily be prepared by methods well known to those skilled in the art from readily available known compounds.

PREPARATIONS AND EXAMPLES

The invention may be more fully understood from the following preparations and examples which are illustrative of the process and compounds of the present invention but are not to be construed as limiting.

Preparation 1: Dehydration of 9α-hydroxyandrostenedione (I) by thionyl chloride (Formula I: $R_6$ and $R_{16}$ are hydrogen)

9α-Hydroxyandrostenedione (U.S. Pat. No. 3,065,146, Example 6; 0.5 g.) is added to pyridine (10 ml.) and cooled to 0°. Thionyl chloride (0.693 g.) is added dropwise keeping the temperature between 0° and 5°. The reaction mixture is stirred at 0°-5° for 20 min. and then distilled water (50 ml.) is added slowly. The pH is adjusted to 2.0 with hydrochloric acid (about 9 ml.). The mixture is cooled to 0°-5° and filtered. The precipitate is washed with distilled water, dried under vacuum at 60° yielding 0.367 g. (78.05% chemical yield). The filtrate is extracted with methylene chloride (2 × 40 ml.). The extract is washed with distilled water, dried and concentrated to dryness, 0.115 g. Total yield is 0.482 g. (102.5% chemical yield). The product is virtually one spot material on TLC (chloroform:methanol, 99:1). GC analysis (3% OU-17, 6 ft., 210°) reveals essentially two peaks whose retention times correspond to known samples of androsta-4,9(11)-diene-3,17-dione and androsta-4,8-diene-3,17-dione. Integration of the 2 peaks show that the two compounds represent 43.4 and 56.0% respectively of the total product.

Preparation 2: Dehydration of 9α-hydroxyandrostenedione (I) by thionyl chloride (Formula I: $R_6$ and $R_{16}$ are hydrogen Following the general procedure of Preparation 1 but making non-critical variations of quantity of thionyl chloride (0.427 g.) and temperature (23°–30°) a crude product, 0.441 g. (93.8% chemical yield) is obtained. GC analysis demonstrates the presence of androsta-4,9(11)-diene-3,17-dione (46.2%) and androsta-4,8-diene-3,17-dione (53.2%).

Preparation 3: Dehydration of 9α-hydroxyandrostenedione (I) by thionyl chloride (Formula I: $R_6$ and $R_{16}$ are hydrogen)

Following the general procedure of Preparation 1 but making non-critical variations, one spot (TLC) product 0.480 g. (102.1% chemical yield) is obtained. GC analysis demonstrates the presence of androsta-4,9(11)-diene-3,17-dione (55.5%) and androsta-4,8-diene-3,17-dione (43.7%).

Preparation 4: Dehydration of 9α-hydroxyandrostenedione (I) by bromine and sulfur dioxide (Formula I: $R_6$ and $R_{16}$ are hydrogen)

9α-Hydroxyandrostenedione (1.0 g.) is added to methylene chloride (10 ml.), stirred and cooled to −15°. A solution of sulfur dioxide (0.8 g.) in pyridine (1 ml.) is added to the steroid mixture and stirred. Next a cold solution of bromine (0.4 ml.) in pyridine (3 ml.) is added to the stirred steroid mixture. The reaction mixture is stirred for 5 min. following which distilled water (10 ml.) is added dropwise maintaining the temperature at about 0°. Following addition of the distilled water, the pH is adjusted to about 2.0 with hydrochloric acid (1N). The methylene chloride layer is separated, washed with water until neutral, dried, and concentrated under vacuum at 50° to yield a crude solid 0.889 g. (94.5% chemical yield). The crude product is analyzed by GC as in Preparation 1, the results demonstrate the presence of androsta-4,9(11)-diene-3,17-dione (about 50%) and androsta-4,8-diene-3,17-dione (about 50%).

Preparation 5: Dehydration of 9α-hydroxyandrostenedione (I) with bromine and sulfur dioxide (Formula I: $R_6$ and $R_{16}$ are hydrogen)

Following the general procedure of Preparation 4 but starting with 0.5 g. of 9α-hydroxyandrostenedione and making non-critical variations 0.491 g. (104.4% chemical yield) of crude product is obtained. GC analysis demonstrates the androsta-4,9(11)-diene-3,17-dione (about 50%) and androsta-4,8-diene-3,17-dione (about 50%).

Preparation 6: Dehydration of 9α-hydroxyandrostenedione (I) by bromine and sulfur dioxide (Formula I: $R_6$ and $R_{16}$ are hydrogen)

A mixture of 9α-hydroxyandrostenedione (2.0 g.), DMF (5.36 ml.) and pyridine (5.36 ml.) is cooled to −15° under nitrogen. A solution of sulfur dioxide (1.7 g.) in pyridine (2 ml.) is added to the steroid mixture. Bromine (0.8 ml.) in pyridine (6 ml.) is then added to the steroid mixture and stirred for 1 hour at −15° to −10°. Distilled water is then added with stirring and cooling. The resulting slurry is cooled to 0° and filtered. The solids are washed with distilled water and dried under vacuum at 80° to give 1.801 g. (95.7% chemical yield) of crude product.

GC analysis, as in Preparation 1, demonstrates the presence of androsta-4,9(11)-diene-3,17-dione (64.4%) and androsta-4,8-diene-3,17-dione (43.7%).

EXAMPLE 1

Androsta-4,9(11)-diene-3,17-dione (Formula III: $R_6$ and $R_{16}$ are hydrogen)

Refer to Chart A.

9α-Hydroxyandrostenedione (5.0 g.) is added to pyridine (20 ml.) and stirred under nitrogen. Phenylsulfinyl chloride (3.5 ml.) is added to the solution with cooling, and stirred at 12°–20° for 45 min. The reaction mixture is then added to a mixture of distilled water (63 ml.) and chloroform (50 ml.) and cooled to 10°. Concentrated aqueous hydrochloride acid (17 ml.) is added while keeping the temperature below 13°. The layers are separated and the aqueous layer is extracted with chloroform (2 × 10 ml.). The chloroform extracts are combined and washed with hydrochloric acid (1N, 10 ml.) and distilled water (15 ml.). The chloroform solution is washed with distilled water (63 ml.), aqueous sodium bicarbonate (3%, 63 ml.) and twice with distilled water (63 ml. each time). The chloroform extracts and the chloroform solution are combined. The chloroform solution is dried over anhydrous magnesium sulfate and concentrated to 75 ml. Silica gel (0.50 g.) and p-TSA (0.05 g.) are added to the chloroform solution and refluxed until the reaction is complete (2¾ hours) as measured by TLC. The reaction mixture is cooled to 50° and filtered. The filtrate is washed with distilled water (63 ml.), aqueous sodium bicarbonate (3%, 63 ml.), twice with distilled water (63 ml. each time), dried over anhydrous magnesium sulfate, and concentrated to dryness. The solid material is stirred with warm (40°–50°) ethyl acetate (20 ml.). SSB (100 ml.) is added to the slurry. The slurry is cooled to 5° and filtered. The solids are washed with SSB and dried under vacuum at 50° to give 3.597 g. (76.49% chemical yield) of androsta-4,9(11)-diene-3,17-dione. The mother liquors are evaporated to dryness. Ethyl acetate (5 ml.) followed by SSB (5 ml.) are added to the residue. The slurry is cooled to 5° and filtered. The solids are washed with SSB and dried under vacuum to give 0.589 g. (12.52% chemical yield) of androsta-4,9(11)-diene-3,17-dione. The total yield is 4.186 g. (89% chemical yield of androsta-4,9(11)-diene-3,17-dione. TLC, $R_f$ = 0.55 (chloroform:ethyl acetate, 75:25).

EXAMPLE 2

Androsta-4,9(11)-diene-3,17-dione (Formula III: $R_6$ and $R_{16}$ are hydrogen)

Refer to Chart A.

9α-Hydroxyandrostenedione (1.0 g.) is dissolved in pyridine (4 ml.) and stirred under nitrogen at 25°. Phenylsulfinyl chloride (0.7 ml.) is added to the solution. The resulting mixture is stirred for 30 min. and then is added slowly to a solution of concentrated aqueous hydrochloric acid (3.5 ml.) in distilled water (50 ml.) at 0°. The resulting slurry is extracted with benzene. The benzene extract is washed once with distilled water, once with a solution of sodium bicarbonate (0.5 g. in 20 ml. of distilled water) and finally twice with distilled water (25 ml. each time), dried over anhydrous magnesium sulfate and concentrated to dryness. The residue is dissolved in benzene (15 ml.). Silica gel (0.1 g.) and p-TSA (0.01 g.) are added to the benzene solution. The resulting mixture is heated at reflux with stirring until the reaction is complete (10 min.) as measured by TLC. The reaction mixture is filtered and the silica gel is washed with benzene. The benzene solution is washed once with water, once with an aqueous sodium bicarbonate (2%, 20 ml.) and twice with distilled water. The benzene solution is dried over anhydrous magnesium sulfate and concentrated to dryness. The crystalline residue is slurried with ethyl acetate (4.0 ml.). SSB (20 ml.) is added slowly to the slurry. The slurry is then cooled to 15° and filtered. The solids are washed with SSB and dried under vacuum at 60° to give 0.787 g. (83.7% chemical yield) of androsta-4,9(11)-diene-3,17-dione. TLC, $R_f$ = 0.55 (chloroform:ethyl acetate, 75:25).

EXAMPLE 3

Androsta-4,9(11)-diene-3,17-dione (Formula III: $R_6$ and $R_{16}$ are hydrogen)

Refer to Chart A.

9α-Hydroxyandrostenedione (9.0 g.) is dissolved in pyridine (36 ml.) and stirred under nitrogen at 25°. Phenylsulfinyl chloride (6.3 ml.) is added slowly to the steroid solution while cooling the reaction mixture to keep the temperature between 23° and 30°. The resulting mixture is stirred for 30 min. and then added to a solution of concentrated aqueous hydrocyloric acid (27 ml.) in distilled water (450 ml.) at 0°. The resulting slurry is extracted with benzene. The benzene extract is washed once with distilled water, once with a solution of sodium bicarbonate (4.5 g. in 180 ml. of distilled water) and twice with distilled water. The benzene solution is dried over anhydrous magnesium sulfate and concentrated at atmospheric pressure to a low volume resulting in a slurry. Ethyl acetate (50 ml.) is added to the slurry. The resulting slurry is concentrated to a small volume and ethyl acetate (50 ml.) is added again. This slurry is concentrated to a low volume, cooled to 10°, and filtered. The solids are washed with ethyl acetate at 0° and dried under vacuum at 60° to give 10.467 g. (82.45% chemical yield) of 9α-hydroxyandrostenedione 9α-phenylsulfinate (II), m.p. 111°–113.5°, $[\alpha]_D$ +3 (chloroform), UV (methanol) $\lambda_{max}$ = 242 mμ ($\epsilon$ = 14,760).

A mixture of 9α-hydroxyandrostenedione 9α-phenylsulfinate (II) (5.64 g.), benzene (60 ml.), silica gel (0.40 g.) and p-TSA (0.04 g.) is heated at reflux until TLC shows that the reaction is complete (10 min.). The reaction mixture is filtered and the silica gel is washed with benzene. The benzene solution is washed once with distilled water (80 ml.), once with aqueous sodium bicarbonate (2%, 80 ml.) and twice with distilled water. The benzene solution is dried over anhydrous magnesium sulfate and concentrated to dryness. The crystalline residue is slurried with ethyl acetate (16 ml.) at 45°–50° and SSB (80 ml.) is slowly added. The slurry is cooled to 10° and filtered. The solids are washed with SSB and dried under vacuum at 70° to give 3.398 g. (90.4% chemical yield of androsta-4,9(11)-diene, 3,17-dione. TLC, $R_f$ = 0.55 (chloroform:ethyl acetate, 75:25).

EXAMPLE 4

Androsta-4,9(11)-diene, 3,17-dione (Formula III: $R_6$ and $R_{16}$ are hydrogen)

Refer to Chart A.

9α-Hydroxyandrostenedione (1 g.) is dissolved in pyridine (4 ml.) and stirred under nitrogen at room temperature. p-Methylphenylsulfinyl chloride (0.8 ml.) is added to the steroid solution. The resulting mixture is stirred for about 30 min. and then added slowly to a solution of concentrated hydrochloric acid (3.5 ml. in 50 ml. of distilled water) at 0°. The resulting slurry is extracted with methylene chloride. The methylene chloride extract is washed once with distilled water, once with an aqueous solution of sodium bicarbonate (2.5%, 20 ml.) and finally with two portions of distilled water (25 ml. each). The methylene chloride solution is dried over anhydrous magnesium sulfate and concentrated to dryness. The residue is redissolved in benzene (15 ml.). Silica gel (0.20 g.) is added and the resulting mixture is then heated at reflux with stirring until TLC shows that the reaction is complete (10 min.). The reaction mixture is filtered and silica gel is washed with benzene. The filtrate is washed once with distilled water, once with an aqueous sodium bicarbonate (2%, 20 ml.) and twice with distilled water. The benzene solution is dried over anhydrous magnesium sulfate and concentrated to dryness. The crystalline residue is slurried with ethyl acetate (4.0 ml.). SSB (20 ml.) is added slowly to this slurry. The slurry is cooled to 15° and filtered. The solids are washed with SSB and dried under vacuum at 60° to give 0.828 g. (88.04% chemical yield) of androsta-4,9(11)-diene-3,17-dione, m.p. 192.5°–201°; $[\alpha]_D$ +214° (chloroform); UV (methanol) $\lambda_{max}$ = 242 mμ ($\epsilon$ = 16,694).

EXAMPLE 5

Androsta-4,9(11)-diene-3,17-dione (Formula III: $R_6$ and $R_{16}$ are hydrogen)

Refer to Chart A.

9α-Hydroxyandrostenedione (5.0 g.) is dissolved in pyridine (20 ml.) and stirred under nitrogen at about 25°. p-Chlorophenylsulfinyl chloride (5.5 ml.) is added to the steroid solution with cooling. The resulting mixture is stirred at 10°–14° for about 1½ hours. The reaction mixture is added to a mixture of distilled water (65 ml.) and chloroform (50 ml.) at 0°. Concentrated aqueous hydrochloric acid (17 ml., pH approximately 2–3) is added to the steroid mixture. The layers are separated and the aqueous layer is extracted with two portions of chloroform (50 ml. each). The chloroform extracts are combined and washed with a solution of hydrochloric acid (1N, 10 ml.) and distilled water (30 ml.). The chloroform solution is then washed with distilled water (50 ml.), aqueous sodium bicarbonate solution (2.5%, 50 ml.) two portions of distilled water. The chloroform extracts are combined with the chloroform solution, dried over anhydrous magnesium sulfate and concentrated to a volume of approximately 75 ml. Silica gel (0.50 g.) and and p-TSA (0.05 g.) are added to the chloroform solution. The resulting mixture is heated at reflux until TLC showed the reaction to be complete (about 4 hours).

During the reflux period some additional reagents are added. After the mixture refluxes for about 2 hours silica gel (0.5 g.) and p-TSA (0.05 g.) are added. The reaction is refluxed for an additional hour, and then silica gel (0.5 g.) is added. When the reaction is complete, as measured by TLC, it is cooled and filtered. The filtrate is washed with distilled water (50 ml.), an aqueous sodium bicarbonate solution (3%, 50 ml.) and two portions of distilled water (50 ml. each), dried over anhydrous magnesium sulfate and concentrated to dryness under reduced pressure. Ethyl acetate (50 ml.) is added to the solids and the resulting slurry is concentrated to dryness under reduced pressure. Ethyl acetate (20 ml.) is added to the residue. The resultant slurry is stirred in a warm water bath (55°) and SSB (100 ml.) is added dropwise with stirring. This slurry is cooled slowly to 10° and filtered. The solids are washed with SSB and dried under vacuum at 50°–60° to give 3.882 g. of crystals, m.p. 175°–195°. A second crop of 0.888 g. of crystals is also obtained. The first crop crystals (3.882 g.) is stirred with ethyl acetate (12 ml.) at 50° for 30 min., cooled to 10° and filtered. The solids are washed with ethyl acetate and then with SSB. The solids are dried under vacuum at 50° to give 2.806 g. of androsta-4,9(11)-diene-3,17-dione, m.p. 198°–201°. TLC, $R_f$ = 0.55 (chloroform:ethyl acetate, 75:25).

EXAMPLE 6

9α-Hydroxyandrostenedione 9-p-chlorophenylsulfinate ester (Formula II: $R_6$ and $R_{16}$ are hydrogen, and R is p-chlorophenyl)

Refer to Chart A.

9α-Hydroxyandrostenedione (2.0 g.) is dissolved in pyridine (8 ml.) and stirred under nitrogen at room temperature. p-Chlorophenylsulfinyl chloride (2.2 ml.) is added to the steroid solution with cooling while keeping the temperature between 10° and 14°. After stirring (about 1 hour) the reaction mixture is added to a cold mixture of distilled water (100 ml.) in methylene chloride (50 ml.). Concentrated aqueous hydrochloric acid (6.0 ml.) which has a pH of about 3 to 4 is added to the mixture. The layers are separated and the aqueous layer is extracted with two 25 ml. portions of methylene chloride. The methylene chloride extracts are combined and washed with a solution of hydrochloric acid (1N, 10 ml.) and distilled water (30 ml.). The methylene chloride solution is then washed with distilled water (50 ml.), an aqueous sodium bicarbonate solution (2.5%, 50 ml.) and two portions of distilled water (50 ml. each). The methylene chloride extracts and solution are combined, dried over anhydrous magnesium sulfate and concentrated to dryness. The residue is stirred with ethyl acetate (10 ml.) for 20 min. at about 25° and then cooled to 10°. This slurry is filtered, the solids washed with ethyl acetate at 0° and dried under vacuum at 40° to give 2.045 g. (67.1% chemical yield) of 9α-hydroxyandrostene-9-p-chlorophenylsulfinate ester, m.p. 122°–123.5°.

EXAMPLE 7

Androsta-4,9(11)-diene-3,17-dione (Formula III: $R_6$ and $R_{16}$ are hydrogen)

Refer to Chart A

Following the general procedure of Examples 1 thru 3, but making non-critical variations but starting with 5 g. of 9α-hydroxyandrostenedione there is obtained 3.618 g. (76.74% chemical yield) of androsta-4,9(11)-diene-3,17-dione.

A second crop of crystals is obtained by concentrating the filtrate and adding ethyl acetate (5 ml.). The mixture is stirred and SSB (5 ml.) is slowly added, stirred for 5 min. and cooled to 10°. The mixture is filtered, the solids washed with SSB, and dried under vacuum at 50° to give 0.698 g. (14.84% chemical yield) of androsta-4,9(11)-diene-3,17-dione.

Therefore, the total yield of androsta-4,9(11)-diene-3,17-dione (first and second crops of crystals) is 91.78%.

With regards to the sulfinylating agent, R—SO—X, halogen atoms refer to chlorine and bromine.

I claim:

1. A chemical process for the preparation of a steroid of the formula:

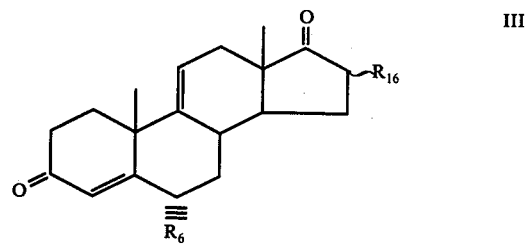

where $R_6$ is a hydrogen or fluorine atom or methyl group; $R_{16}$ is a hydrogen atom or methyl group and where ~ indicates the attachment of the $R_{16}$ group is in the α or β configuration which comprises (1) sulfinylating a 9α-hydroxy steroid of the formula:

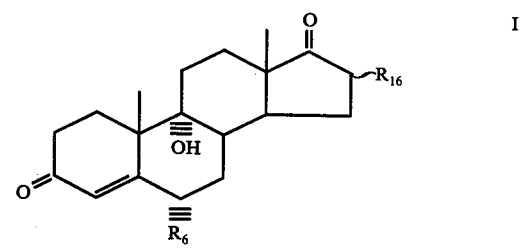

where $R_6$, $R_{16}$, and ~ are defined above with a sulfinylating agent of the formula R—SO—X where R is alkyl of 1 through 4 carbon atoms, or phenyl substituted with 0–3 substituents which may be the same or different and are selected from the group consisting of halogen atoms, or methyl, ethyl or nitro groups and where X is a chlorine or bromine atom to form a sulfinate ester of the formula:

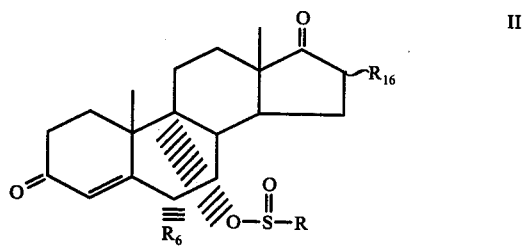

and (2) desulfinylating the sulfinate ester (II) by heating to at least 40° in the presence of a support catalyst selected from the group consisting of silica gel or alumina and an acid whose pKa is less than or equal to 5.0.

2. A process according to claim 1 where the support catalyst is silica gel.

3. A process according to claim 2 where the sulfinylating agent is selected from the group consisting of phenylsulfinyl chloride, p-methylphenylsulfinyl chloride and p-chlorophenylsulfinyl chloride and the acid is selected from the group consisting of phenylsulfonic acid, p-methylphenylsulfonic acid (p-TSA), and p-chlorophenylsulfonic acid.

4. A process according to claim 3 where the sulfinylating agent is phenylsulfinyl chloride and the acid is p-methylphenylsulfonic acid (p-TSA).

5. A process according to claim 4 where the steroid (III) is androsta-4,9(11)-diene-3,17-dione.

6. A process according to claim 4 where the steroid (III) is 6α-methylandrosta-4,9(11)-diene-3,17-dione.

7. A process according to claim 4 where the steroid (III) is 6α-fluoroandrosta-4,9(11)-diene-3,17-dione.

8. A chemical process for the preparation of a sulfinate ester of the formula:

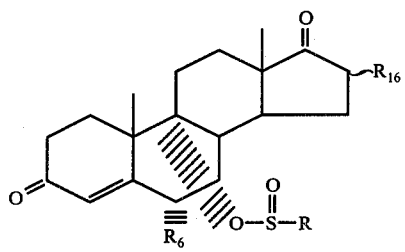

II which comprises sulfinylating a 9α-hydroxy steroid of the formula:

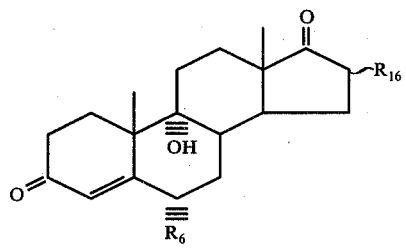

I with a sulfinylating agent of the formula R—SO—X where $R_6$, $R_{16}$, ~, R, and X are defined in claim 1.

9. A process according to claim 8 where the sulfinylating agent is selected from the group consisting of phenylsulfinyl chloride, p-methylphenylsulfinyl chloride and p-chlorophenylsulfinyl chloride.

10. A process according to claim 9 where the sulfinylating agent is phenylsulfinyl chloride.

11. A process according to claim 10 where the 9α-hydroxy steroid (I) is 9α-hydroxyandrostenedione.

12. A process according to claim 10 where the 9α-hydroxy steroid (I) is 6α-methyl-9α-hydroxyandrostenedione.

13. A process according to claim 10 where the 9α-hydroxy steroid (I) is 6α-fluoro-9α-hydroxyandrostenedione.

14. A chemical process for the preparation of a steroid of the formula:

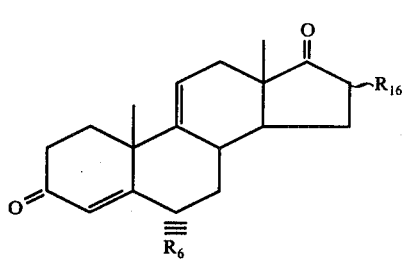

III which comprises desulfinylating a sulfinate ester of the formula:

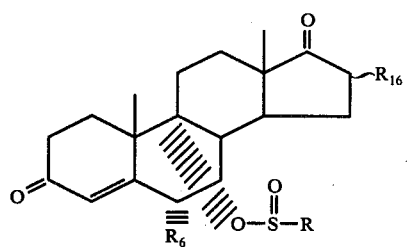

II by heating to at least 40° in the presence of a support catalyst and an acid whose pKa is less than or equal to 5.0 where $R_6$, $R_{16}$, ~, R, and support catalyst are defined in claim 1.

15. A process according to claim 14 where the support catalyst is silica gel.

16. A process according to claim 15 where the acid is selected from the group consisting of phenylsulfonic acid, p-methylphenylsulfonic acid (p-TSA), and p-chlorophenylsulfonic acid.

17. A process according to claim 16 where the acid is p-methylphenylsulfonic acid (p-TSA).

18. A process according to claim 17 where the steroid (III) is androsta-4,9(11)-diene-3,17-dione.

19. A process according to claim 17 where the steroid (III) is 6α-methylandrosta-4,9(11)-diene-3,17-dione.

20. A process according to claim 17 where the steroid (III) is 6α-fluoroandrosta-4,9(11)-diene-3,17-dione.

21. A sulfinate ester of the formula:

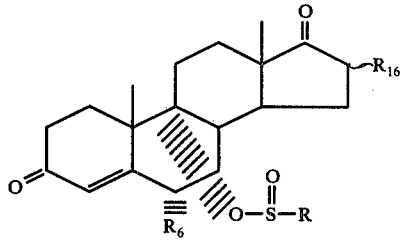

II where R, $R_6$, $R_{16}$ and ~ are defined in claim 1.

22. A sulfinate ester according to claim 21 which is 9α-hydroxyandrostenedione 9α-phenylsulfinate.

23. A sulfinate ester according to claim 21 which is 6α-methyl-9α-hydroxyandrostenedione 9α-phenylsulfinate.

24. A sulfinate ester according to claim 21 which is 6α-fluoro-9α-hydroxyandrostenedione 9α-phenylsulfinate.

25. A chemical process for the preparation of $\Delta^{9(11)}$-androstenedione (III) which comprises:
  (1) sulfinylating 9α-hydroxyandrostenedione (I) with phenylsulfinyl chloride to form 9α-hydroxyandrostenedione 9α-phenylsulfinate (II) and
  (2) desulfinylating 9α-hydroxyandrostenedione 9α-phenylsulfinate (II) by heating to at least 40° in the presence of silica gel and p-methylphenylsulfonic acid (p-TSA).

* * * * *